United States Patent [19]
Dias et al.

[11] Patent Number: 5,400,788
[45] Date of Patent: Mar. 28, 1995

[54] APPARATUS THAT GENERATES ACOUSTIC SIGNALS AT DISCRETE MULTIPLE FREQUENCIES AND THAT COUPLES ACOUSTIC SIGNALS INTO A CLADDED-CORE ACOUSTIC WAVEGUIDE

[75] Inventors: J. Fleming Dias, Palo Alto; Hewlett E. Melton, Jr., Sunnyvale, both of Calif.

[73] Assignee: Hewlett-Packard, Palo Alto, Calif.

[21] Appl. No.: 72,828

[22] Filed: Jun. 7, 1993

Related U.S. Application Data

[63] Continuation-in-part of Ser. No. 352,517, May 16, 1989, Pat. No. 5,217,018, and a continuation of Ser. No. 918,298, Jul. 22, 1992, Pat. No. 5,284,148.

[51] Int. Cl.$^6$ .............................................. A61B 8/00
[52] U.S. Cl. ............................. 128/662.03; 128/662.06
[58] Field of Search ...................... 128/662.06, 662.03; 333/149, 147; 385/7, 123

[56] References Cited

U.S. PATENT DOCUMENTS

| | | | |
|---|---|---|---|
| 3,654,574 | 4/1972 | Dias | 330/30 |
| 3,777,189 | 12/1973 | Skinner et al. | 333/149 |
| 3,922,622 | 11/1975 | Boyd et al. | 333/147 |
| 4,063,198 | 12/1977 | Wagners et al. | 330/30 R |
| 4,077,023 | 2/1978 | Boyd et al. | 310/365 |
| 4,276,491 | 6/1981 | Daniel | 128/662.03 |
| 4,742,318 | 5/1988 | Jen et al. | 333/147 X |
| 4,743,870 | 5/1988 | Jen et al. | 333/149 X |
| 4,870,972 | 10/1989 | Maerfeld et al. | 128/662.03 |
| 4,894,806 | 1/1990 | Jen et al. | 367/7 |
| 5,152,291 | 10/1992 | Dias | 128/661 |
| 5,217,018 | 6/1993 | Dias | 128/662.06 |
| 5,284,148 | 2/1994 | Dias et al. | 128/662.06 |

OTHER PUBLICATIONS

Don E. Bray et al., NONDESTRUCTIVE EVALUATION, pp. 58–68, McGraw-Hill.
E. Ash et al., "Acoustic Bulk-Surface Wave Transducer", Electronic Letters, vol. 5, No. 9, 1 May 1969, pp. 175–176.
A. Safaai-Jazi et al., "Longitudinal Modes in Weakly Guiding Fiber Acoustic Waveguides", 1985 Ultrasonics Symposium, Oct. 16–18, Cathedral Hill, SF, CA.

*Primary Examiner*—Francis Jaworski

[57] ABSTRACT

Spherical annulus piezoelectric transducers 62, 64 and spherical disc piezoelectric transducer 66 form a spherical shell having a radius of curvature R with a focal point 70 near the end of cladded-core acoustic waveguide 72. Each transducer 62, 64, 66 generates a bulk acoustic wave of a unique frequency and transmits it to focal point 70 where it enters core 74 of cladded-core acoustic waveguide 72. Alternatively, a conical annulus piezoelectric transducers 92, 116 on a prism 90 generate bulk acoustic waves of multiple discrete frequencies and focus them through cladding 75 and into core 74 of cladded-core acoustic waveguide 72. Surface acoustic waves of multiple discrete frequencies can be generated by multiple sets of curvilinear interdigital conductors 132, 134 on a piezoelectric substrate 122. The shape of curvilinear interdigital conductors 132, 134 focuses the surface acoustic waves at focal point 70 located near the end of acoustic waveguide 72. The surface acoustic waves are converted into bulk/longitudinal waves by either curvilinear corrugations 142, 146 or by a coupling medium that causes the surface acoustic waves to become leaky longitudinal waves. Alternatively, the surface acoustic waves can be coupled to the core of the acoustic waveguide by converting them into either bulk/longitudinal waves or leaky longitudinal waves and guiding them through the cladding to the core. When the acoustic signals travel through the cladding to couple to the core, the acoustic waveguide can transmit optical signals.

23 Claims, 7 Drawing Sheets

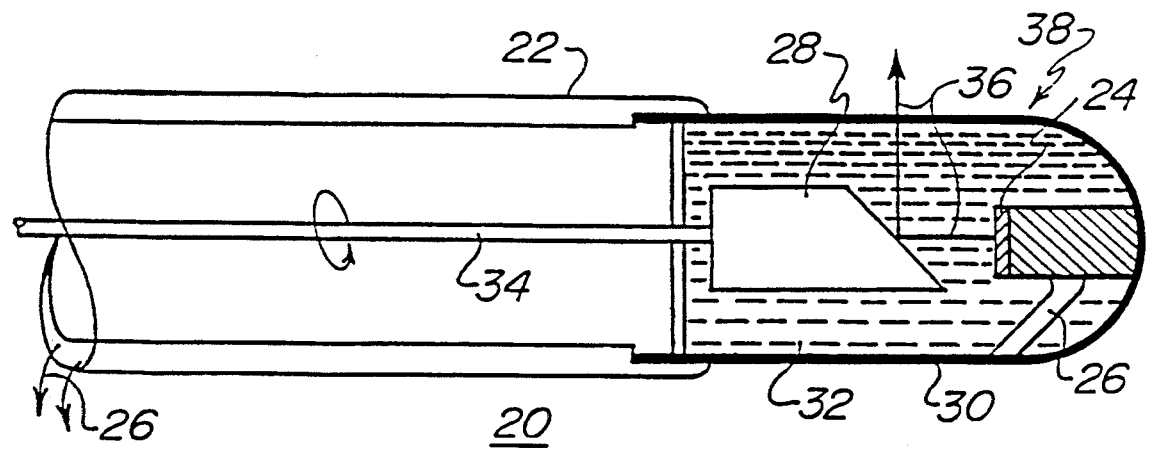
Figure 1 (Previously Known)
Figure 2 (Previously Known)
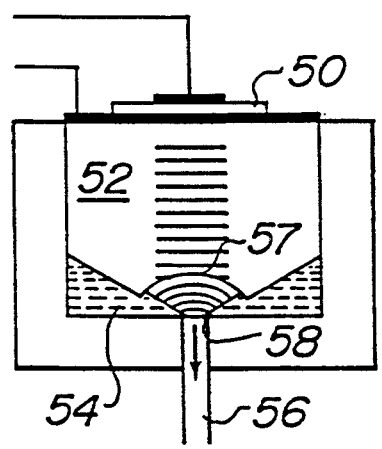
Figure 3 (Previously Known)

APPARATUS THAT GENERATES ACOUSTIC SIGNALS AT DISCRETE MULTIPLE FREQUENCIES AND THAT COUPLES ACOUSTIC SIGNALS INTO A CLADDED-CORE ACOUSTIC WAVEGUIDE

CROSS-REFERENCE TO RELATED APPLICATIONS

This is a continuation-in-part of application, filed on May 16, 1989, having the Ser. No. 07/352,517, issued on 8 Jun. 1993 as U.S. Pat. No. 5,217,018, entitled *Acoustic Transmission Through Cladded Core Waveguide* (previously entitled An Ultrasonic Catheter Guidance System), filed in the name of J. Fleming Dias, and owned by the assignee of this application and incorporated herein by reference. Also, this application is a continuation-in-part of another application, filed Jul. 22, 1992, having Ser. No. 07/918,298, issued on 8 Feb. 1994 as U.S. Pat. No. 5,284,148, entitled *Intracavity Ultrasound Diagnostic Probe Using Fiber Acoustic Waveguides*, filed in the name of J. Fleming Dias and Hewlett E. Melton, Jr., and owned by the assignee of this application and incorporated herein by reference.

BACKGROUND OF THE INVENTION

1. Field of the Invention

The invention relates generally to the field of ultrasound diagnostic probes and more specifically to the field of invasive ultrasound diagnostic probes.

2. Description of Related Art

FIG. 1 shows the basic construction of a previously known ultrasound diagnostic probe. The imaging probe 20 consists of a catheter 22, a piezoelectric transducer 24 (i.e., a transducer having a material that electrically polarizes when mechanically strained and that mechanically strains when electrically polarized) at the distal end 38 of the catheter (i.e., the end of the catheter that goes into the body), electric wires 26 that connect piezoelectric transducer 24 to external circuitry at the proximal end (i.e., the end that stays outside the body), an acoustic reflector 28 (i.e., a mirror) at the distal end, a rotating drive shaft 34 coupled to a small motor/shaft encoder at the proximal end, and a plastic radome 30 (i.e., an acoustic window that has the same acoustic impedance as a fluid) filled with a liquid 32 that fits over piezoelectric transducer 24 and acoustic reflector 28.

Piezoelectric transducer 24 is stationary and when excited by an external source, it produces an acoustic signal 36 that travels through the liquid in radome 30 and strikes acoustic reflector 28. The surface of acoustic reflector 28 resides at an angle of 45° from acoustic signal 36 and it reflects acoustic signal 36 at an angle of 90° from its original path. The reflected acoustic signal 36 travels through liquid 32 in radome 30 and propagates through the blood until it encounters the arterial wall.

Depending on the penetration into the arterial wall, several echoes return to piezoelectric transducer 24 by retracing essentially the same path. Piezoelectric transducer 24 converts these echoes into corresponding electrical pulses and wires 26 carry these electrical pulses to electrical circuitry located at the proximal end. Since acoustic reflector 28 continuously rotates, acoustic signal 36 continuously rotates. Echoes from each angular position are collected, processed and displayed on a CRT screen.

Previously known imaging probes have variations of the configuration shown in FIG. 1. In one alternate configuration, the acoustic reflector 28 and piezoelectric transducer 24 exchange places and in another alternate configuration, the reflector is omitted and the transducer is attached directly to the rotating shaft. These and other configurations have the following in common: all use a piezoelectric transducer at the distal end of the catheter, which goes inside the body, and generates a single frequency signal.

Placing the piezoelectric transducer at the distal end of the catheter that goes inside the body has numerous disadvantages. The piezoelectric transducer may emit leakage currents inside the body that can induce fibrillation when the probe images a coronary artery. Wires 26 that connect the piezoelectric transducer to external circuitry inherently act as antennas and they receive radio frequency (RF) interference present in a catheterization laboratory. This RF interference appears as noise in the electrical signals that travel to and from the piezoelectric transducer and increases the risk of fibrillation induced by the electrical signals.

Another disadvantage of placing the piezoelectric transducer at the distal end of the catheter is that after one use the piezoelectric transducer must be discarded along with the catheter to prevent the transmission of disease. This is burdensome because the piezoelectric transducers are difficult and expensive to make. It also discourages use of the most desirable transducers because they usually are more expensive. Generally, increasing the frequency of the acoustic waves improves the resolution capability of the transducer, but it also increases the expense because the output frequency of piezoelectric transducers depends upon their thickness (i.e., a 40 MHz piezoelectric transducer would have a thickness of approximately 0.05 mm) and the thinner the transducer, the more expensive the transducer.

Another disadvantage of placing the piezoelectric transducer at the distal end is that the piezoelectric transducer can only produce an acoustic signal of a single frequency. The user cannot adjust the piezoelectric transducer to obtain an acoustic signal of another frequency that will give a more desirable resolution or that illuminates a particular region of interest.

Parent patent application having Ser. No. 07/918,298, entitled *Intracavity Ultrasound Diagnostic Probe Using Fiber Acoustic Waveguides*, and incorporated by reference above, describes an ultrasound diagnostic probe that is a cladded-core acoustic waveguide. An acoustic waveguide typically has a central core and an outer cladding that surrounds the core. The purpose of the cladding is to confine the acoustic signals within the central core. When the materials for the cladding and the core meet the specifications described in patent application Ser. No. 07/918,298, the fiber guides the acoustic signals because they bounce off the cladding and stay inside the core.

FIG. 2 shows a previously known piezoelectric transducer 40 that is bonded to the flat end of acoustic waveguide 42 so that an acoustic signal 44 is directly coupled into acoustic waveguide 42. One problem with this configuration is that acoustic waveguides 42 are very small, approximately 0.5 mm and it is very difficult to glue a transducer to them. Another problem with this configuration is that the size of piezoelectric transducer 40 scales inversely with frequency. For example, a piezoelectric transducer 40 that produces a 40 MHz signal has a thickness around 0.05 mm (2 mils). Thus, the fabrication of this device on a production basis presents many difficulties.

FIG. 3 shows an apparatus disclosed in C. K. Jen, Ahmad Safoai-Jazi, Gerald Farnel "Leaky Modes in Weakly Guiding Fiber Acoustic Waveguides" *IEEE Transactions on Ultrasonics, Ferroelectrics and Frequency Control*, Vol. UFFC-33, No. 6, Nov. 1986, pg. 634 and U.S. Pat. No. 4,743,870 by Jen et al. This device generates a single frequency acoustic signal created by a piezoelectric transducer 50 and couples it to an acoustic waveguide 56 through a buffer rod 52 and a liquid coupling medium 54. When the acoustic signal strikes dimple 57 on buffer rod 52, this spherically curved surface focuses the energy of the acoustic wave very close to an end 58 of acoustic waveguide 56 and the acoustic signal enters acoustic waveguide 56. This arrangement has several coupling interfaces and higher coupling losses can be expected. The relatively high attenuation in blood and the proximal part of the arterial wall (i.e., the inner layers of the artery) cause the returning echoes from an intravascular imaging catheter to be small to begin with and any additional coupling losses will reduce the dynamic range of the imaging system. Another problem with this arrangement is that the frequency of the acoustic wave cannot be altered.

It is desirable to efficiently couple acoustic signals to a cladded-core acoustic waveguide and to change the frequency of the probing acoustic signal without replacing the catheter and the transducer. For example, when using a catheter tip doppler probe (i.e., a transducer attached at the tip of the catheter), it is desirable to change the frequency of the acoustic signal depending on the blood flow velocity. When using a cladded-core acoustic waveguide to image an arterial wall, it is necessary to have different frequencies to see different layers on the inside of the blood vessel, to resolve the medial layer, to differentiate between the different layers that form an occlusion such as thrombus (i.e., the top layer of plaque), soft plaque (i.e., the bottom layer of plaque), and probably to differentiate between stable and unstable plaque.

SUMMARY OF THE INVENTION

The present invention includes: piezoelectric transducers that generate bulk/longitudinal waves (i.e., a longitudinal wave that travels through the bulk of the acoustic waveguide) at multiple-discrete frequencies, piezoelectric transducers that generate surface acoustic waves at multiple-discrete frequencies, and devices for coupling these acoustic waves directly to the core of an acoustic waveguide. Also, the present invention includes devices for coupling bulk/longitudinal acoustic waves and SAW acoustic waves to the core of the acoustic waveguide by guiding them through the cladding.

The present invention includes a cladded-core acoustic waveguide, a first piezoelectric transducer having a shape and polarization that focuses the acoustic signal it generates at the end of the cladded-core acoustic waveguide, and a second piezoelectric transducer having a shape and a polarization that focuses the acoustic signal it generates at the end of the cladded-core acoustic waveguide. The piezoelectric transducers can be spherical annulus transducers, each generating an acoustic signal of a different frequency, with a common focal point at the end of the cladded-core acoustic waveguide.

Alternatively, the piezoelectric transducers can be multiple sets of curvilinear interdigital conductors on a piezoelectric substrate, each set generating a surface acoustic wave of a different frequency. The surface acoustic waves are converted into bulk (longitudinal) acoustic waves by either multiple sets of curvilinear corrugations or by a coupling medium, such as a soft epoxy, that causes surface acoustic waves to become leaky longitudinal waves. A tapered guide funnels these leaky waves into the core of the acoustic waveguide. The present invention can have an optical port so that the device can transmit acoustic waves as well as light waves, if a collinear interaction between these waves is desirable. Moreover, the optical port can be replaced with a broad band acoustical receiver, to receive echoes from an imaging or Doppler velocity probe.

In addition to coupling the bulk/longitudinal acoustic waves and the surface acoustic wave directly into the core of the cladded-core acoustic waveguide, the present invention can couple these waves to the core by first guiding them through the cladding. Advantages of this configuration include: the ability to couple a higher-power acoustic signal to the acoustic waveguide and the ability send optical signals through the acoustic waveguide. These devices have a cladded-core acoustic waveguide, one or more piezoelectric transducers circling a portion of the cladded-core acoustic waveguide, and a coupling medium that guides the acoustic waves through the cladding and into the core of the acoustic waveguide. Piezoelectric transducers that generate bulk (longitudinal) waves are positioned on the coupling medium so that the bulk waves travel through the coupling medium at an angle that results in their coupling to the core. If the piezoelectric transducer is the type that generates surface acoustic waves (i.e., SAW's), the coupling medium is either corrugations that convert surface acoustic waves into bulk/longitudinal waves or a coupling medium that causes some of the surface acoustic waves to become leaky longitudinal waves that it guides to the core of the acoustic waveguide. These devices can have an optical port so that it can transmit acoustic waves as well as light waves, if a collinear interaction between these waves is desirable. Moreover, the optical port can be replaced by a broad band acoustical receiver, to receive echoes from an imaging or Doppler velocity probe.

Brief Description of the Drawings

FIG. 1 shows a previously known ultrasonic imaging catheter with a single frequency piezoelectric transducer located inside it.

FIG. 2 shows a previously known single frequency piezoelectric transducer coupled to an acoustic fiber.

FIG. 3 shows a previously known single frequency piezoelectric transducer coupled to an acoustic fiber.

DETAILED DESCRIPTION OF THE INVENTION

Figure 4:
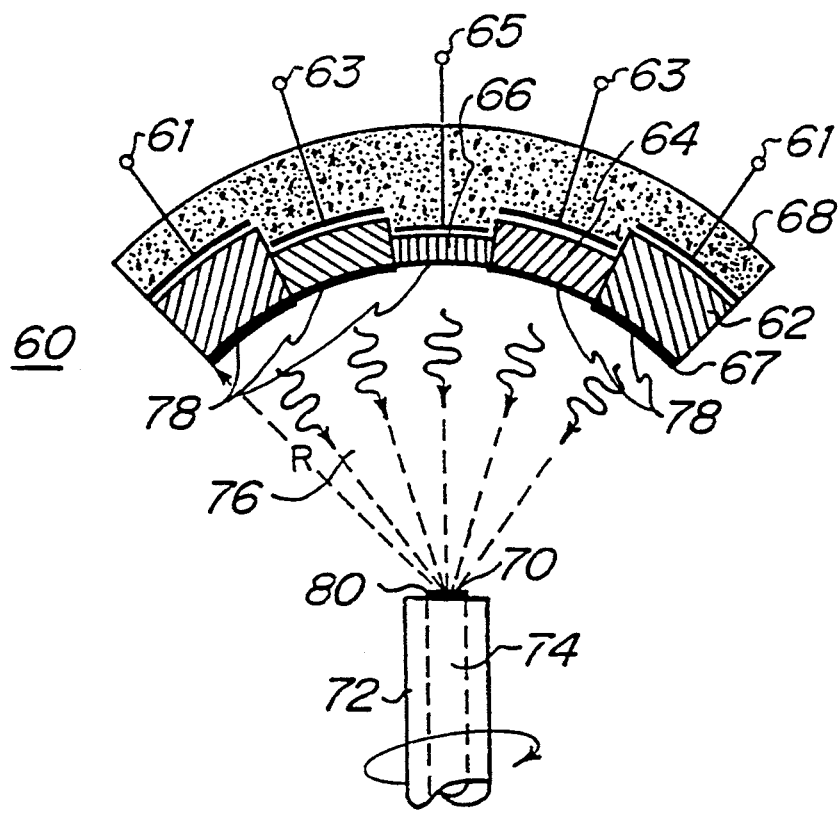
FIG. 4 shows a cross-section of an array of piezoelectric transducers in the shape of spherical annuli, each annulus having a different thickness so that each annulus produces an acoustic signal with a different frequency.

FIG. 4 shows a cross-section of an array of piezoelectric transducers 60 in the shape of spherical annuli. Spherical annulus transducers 62, 64 and spherical disc transducer 66 form a spherical shell having a radius of curvature R with a focus point 70 at the end of acoustic fiber. The application of an electric field across each electrode 61, 63, 65 and a ground electrode 67 that runs along matching layer 78 polarizes each spherical annulus transducer 62, 64 and spherical disc transducer 66 so that the acoustic signals they generate travel in a radial direction from each spherical transducer. The spherical shape and the polarization of each spherical annulus transducer 62, 64 and spherical disc transducer 66 causes them to focus the acoustic energy they generate at a focal point 70 that is adjacent to a core 74 of an acoustic fiber 72.

Piezoelectric transducers resonant at a frequency, $f_0$, having a wavelength, $\lambda_0$, that is two times the thickness of the transducer. Frequency, $f_0$, and the wavelength, $\lambda_0$, are related to one another by the equation $f_0 \lambda_0 = V_L$, where $V_L$ is the speed of bulk-longitudinal acoustic waves in that material. By solving for $\lambda_0$ and substituting $\lambda_0 = 2t$ into that equation, the thickness of the transducers 62, 64, 66 equals $$t = \frac{V_L}{2f_0}.$$

This equation tells us that the thicker spherical disc transducer 66 or spherical annulus transducers 62, 64 are, the lower their resonant frequency will be. Each transducer 62, 64, 66 has a different thickness, and each transducer 62, 64, 66 is driven at its resonant frequency (through electrodes 61, 63, 65 and a ground electrode 67) so that each transducer generates an acoustic signal having a different frequency. In the case of an array of piezoelectric transducers 60 shown in FIG. 4, the center spherical disc transducer 66 transmits the highest frequency signal and outer spherical annulus transducer 62 transmits the lowest frequency signal.

Annuli that produce acoustic signals in the lower frequency range (i.e., 10 to 20 MHz), can be constructed from a piezoelectric like PZT. If the annuli are to produce higher frequency signals, then they must be constructed from another material because construction with PZT becomes too labor intensive. Depending on the application, several piezoelectric materials like zinc oxide, PVDF copolymer and PZT films sputtered or made by Sol-Gel process can be substituted.

When the piezoelectric material is excited, it sends out acoustic waves in all directions. To obtain short and well behaved pulses, the convex part of array of spherical annuli 60 is covered by an acoustic absorber 68 of comparable acoustic impedance to disc 66 and spherical annuli 62, 64. An example of an acoustic absorber is epoxy mixed with teflon powder and fine tungsten powder. Acoustic absorber 68 produces well behaved pulses because the energy from one face is partially absorbed by the acoustic absorber and the multiple reflections through the transducer are reduced. To optimize, one has to use the Mason equivalent circuit for the transducer design.

Spherical disc 66 and each spherical annulus 62, 64 have a matching layer 78 whose thickness is inversely proportional to the frequency of the acoustic signal produced. Specifically, the thickness equals $V_{ML}/4f_0$. The inner surface of the sphere formed by array of piezoelectric transducers 60 is a smooth spherical surface. Matching layer 78 is formed by spinning, spraying, or silk-screening the matching layer on the inner surface of the sphere and pressing a mandrel against it that forming matching layer 78 with different thickness spherical annuli that are aligned with spherical annuli transducers 62, 64 and spherical disc transducer 66. The material for the matching layer is made by mixing an epoxy of suitable viscosity with 1 to 3 microns of aluminum oxide powder. Details for fabricating this type of matching layer is described in U.S. Pat. No. 5,025,790 which issued in 1991 to Dias and is assigned to the assignee of this application and is incorporated herein by reference.

A matching layer 80 for the acoustic waveguide 72 would be shaped with either a flat or spherical surface facing spherical disc 66 and spherical annuluses 62, 64. The end of acoustic waveguide 72 is normally flat but it could be made spherical with a spherically-shaped jig. The spherically shaped end of acoustic waveguide 72 would concentrate the acoustic waves inside the core 74 of the acoustic waveguide 72. The drawings show acoustic waveguide 72 with a flat end. The flat end is a special case of the spherical shape with an infinite radius of curvature.

Matching layer 80 must match the impedance of either a fluid coupler 76, solid coupler 82, or small fluid coupler 84 to acoustic waveguide 72 for a broad band of frequencies produced by the array of spherical annuli 60. Also, matching layer 80 can help protect the acoustic waveguide from cavitation caused by high intensity acoustic energy. Matching layer 80 could consist of a single layer that is not optimal for any single frequency produced by the array of spherical annuli 60 but it is a good compromise for all the frequencies produced. Alternatively, matching layer 80 could consist of several layers, each layer having a different acoustic impedance, so that matching layer 80 is a broadband matching layer that will improve the impedance matching of the coupling means to acoustic waveguide 72. Array of spherical annuli 60 and acoustic waveguide 72 should be enclosed in a hermetically sealed container. Provisions will be made to avoid any bubbles from forming on the fiber or the transducer due to outgassing of the liquid coupler (i.e., liquid coupler has dissolved gases that come out as bubbles due to the rotation of the imaging acoustic waveguide 72). FIG. 4 shows a liquid coupling 76 between the array of spherical annuli 60 and acoustic waveguide 72.

Figure 5:
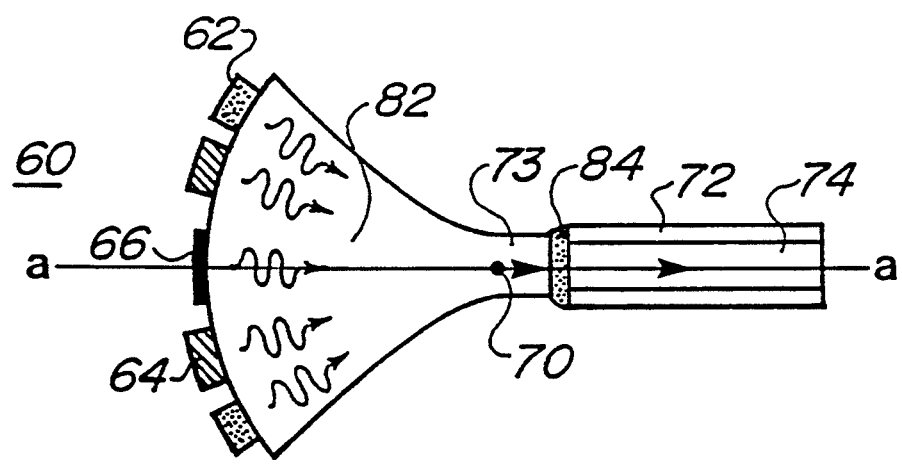
FIG. 5 shows a cross-section of a solid horn directly attached to the array of piezoelectric transducers having the shape of the spherical annuli on one side and the acoustic waveguide at the other end.

FIG. 5 shows a cross-section of horn 82 (e.g., longitudinal vibrator) between the array of piezoelectric transducers 60 and acoustic waveguide 72. Horn 82 is a solid of revolution about an axis a—a. Acoustic energy is focused at focal point 70 at the entry of cylindrically-shaped tip section 73. At focal point 70, the acoustic wave is almost a plane wave and couples easily into tip section 73. Spherical disc transducer 66 and spherical annuli transducers 62, 64 are permanently attached to horn 82. Horn 82 can be metallic or nonmetallic. The impedance mismatch at the transducer/horn interface and the horn/fiber interface is adjusted using suitable matching layers. Horn 82 could also be designed on principles given by Mason in *Physical Acoustics*, Vol. 1, Part B, page 253-363.

If acoustic waveguide 72 is permanently attached to horn 82, either acoustic waveguide 72 will not rotate or the entire structure including array of spherical annuluses 60, horn 82, and acoustic waveguide 72 will rotate. If only acoustic waveguide 72 rotates, then an small fluid coupling 84 exists between horn 82 and acoustic waveguide 72.

Figure 6:
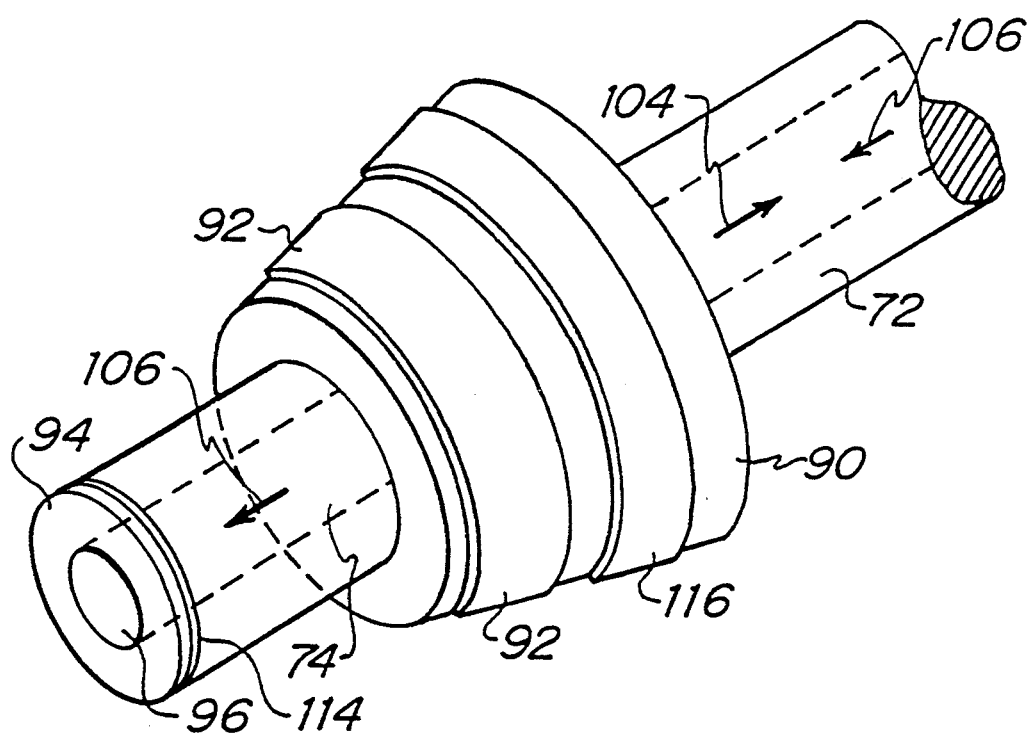
FIG. 6 shows a bulk (longitudinal) device that generates acoustic waves of multiple frequencies and couples them into the core of the acoustic waveguide by transmitting them through the cladding.
Figure 7:
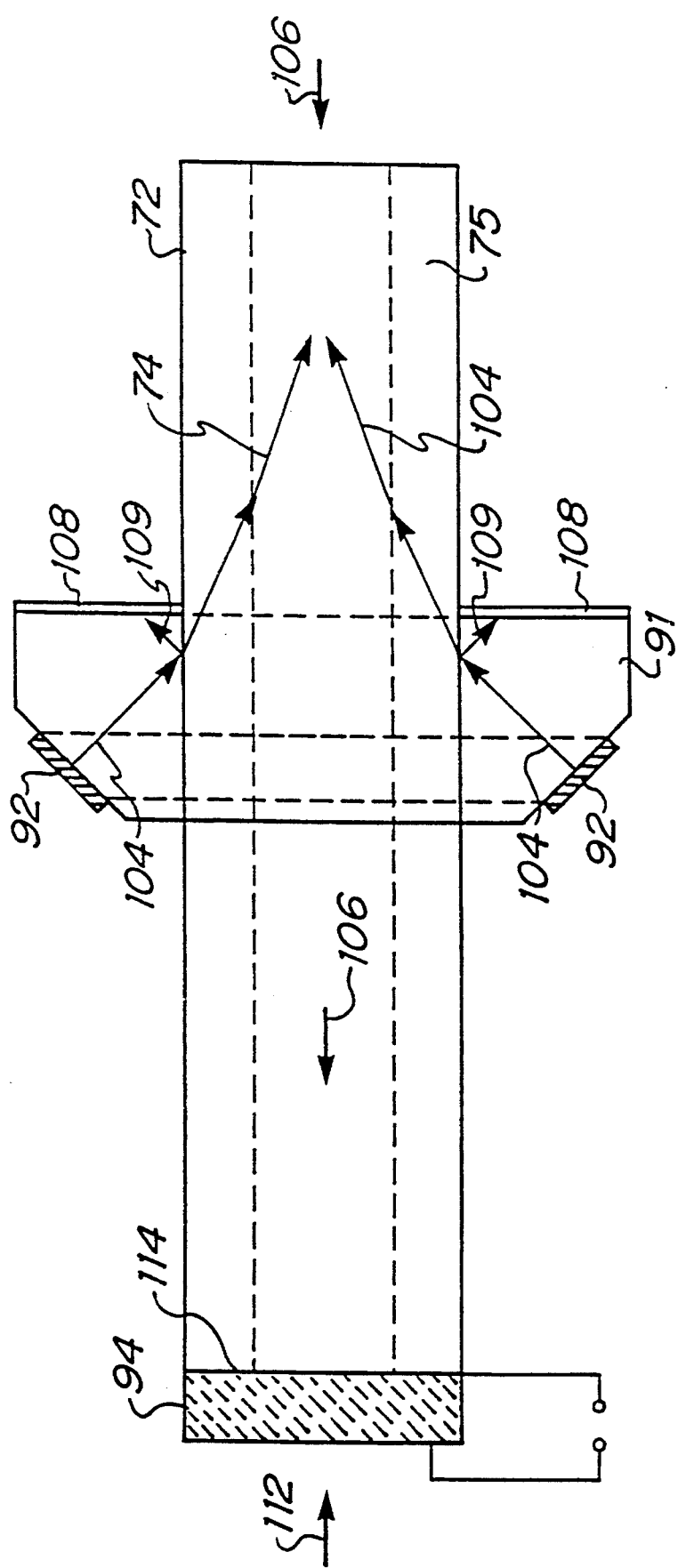
FIG. 7 shows a cross-section of the device shown in FIG. 6.

FIG. 6 is a perspective drawing and FIG. 7 is a cross-sectional drawing of a device that generates bulk/longitudinal acoustic waves 104 and that guides these acoustic waves through cladding 75 to couple them to core 74 of acoustic waveguide 72. A piezoelectric transducer ring 92 wraps around a coupling prism 90, 91 (coupling prism 90, shown in FIG. 6, is identical to coupling prism 91, shown in FIG. 7, except that prism 90 has a second piezoelectric transducer ring 116) and emits bulk/longitudinal acoustic waves 104 that travel through coupling prism 90, 91 to acoustic waveguide 72. In the preferred embodiment of the invention, the prism is constructed from a material have low attenuation at high frequencies. Additional, prism 90, 91 has a conical shape and piezoelectric transducer ring 92 is a conical annulus.

The velocity of acoustic wave 104 in acoustic waveguide 72, 4,500 m/sec, is greater than the velocity of acoustic wave 104 in prism 91, so part of the energy of acoustic wave 104 reflects to form a shear wave 109. Acoustic absorber 108 absorbs shear wave 109. Acoustic absorber 108 is made in the same way and from the same material as acoustic absorber 68 in FIG. 4. Additionally, the direction of acoustic wave 104 changes slightly as can be predicted from Snell's Law. Since the velocity of acoustic wave 104 in cladding 75 is similar to the velocity of acoustic wave 104 in core 74, the direction of acoustic wave 104 does not vary significantly when it passes through this interface. As shown in FIG. 6, transducer 92 goes all the way around acoustic waveguide 72. This causes the acoustic beam to come out in the shape of a cone.

Echo acoustic signal 106 has reflected off the body tissue and is traveling inside the core of acoustic waveguide 72 to a broad band receiver 94. In the preferred embodiment this broad band receiver 94 is made from P(VDF - TrFE) which is an organic piezoelectric material. As shown in FIG. 6, a spot electrode 96 for broad band receiver 94 has a diameter that equals the diameter of the core 74 of acoustic waveguide 72. A matching layer 114 matches the acoustic impedance of core 74 and broad band receiver 94. An optical beam 112 can be transmitted by acoustic waveguide 72 by not installing broadband receiver 94 onto acoustic waveguide 72 and by inserting and optical beam 112 into one end of acoustic waveguide 72 and transmitting it through core 74. In this case, the broadband receiver 94 would be replaced by an optical laser signal.

Figure 8:
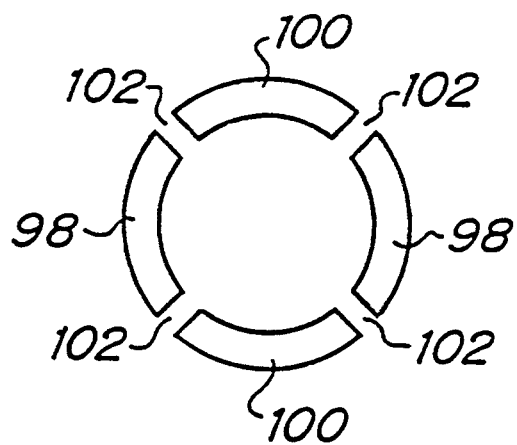
FIG. 8 shows how the piezoelectric transducer can be divided to generate multiple acoustic signals with different frequencies.

Coupling prism 90, as shown in FIG. 6, has a second piezoelectric transducer ring 116 for generating an acoustic signal having a different frequency than that belonging to the acoustic signal produced by piezoelectric transducer ring 92. Alternate embodiments of the invention may have additional segmental piezoelectric transducer rings as shown in FIG. 8 without departing from the scope of the invention. With the additional ring(s), the user can switch the frequency of acoustic wave 104.

FIG. 8 is a cross-sectional drawing of a multi-frequency piezoelectric transducer ring 92 that has two pairs of piezoelectric transducers 98, 100 where each pair generates bulk/longitudinal acoustic waves having a different frequency so that the user can change the frequency of bulk/longitudinal acoustic wave 104. Alternate embodiments of the invention may have several multi-frequency piezoelectric transducer rings 92 or segmental rings 98 and 100 on one prism 90.

Figure 9:
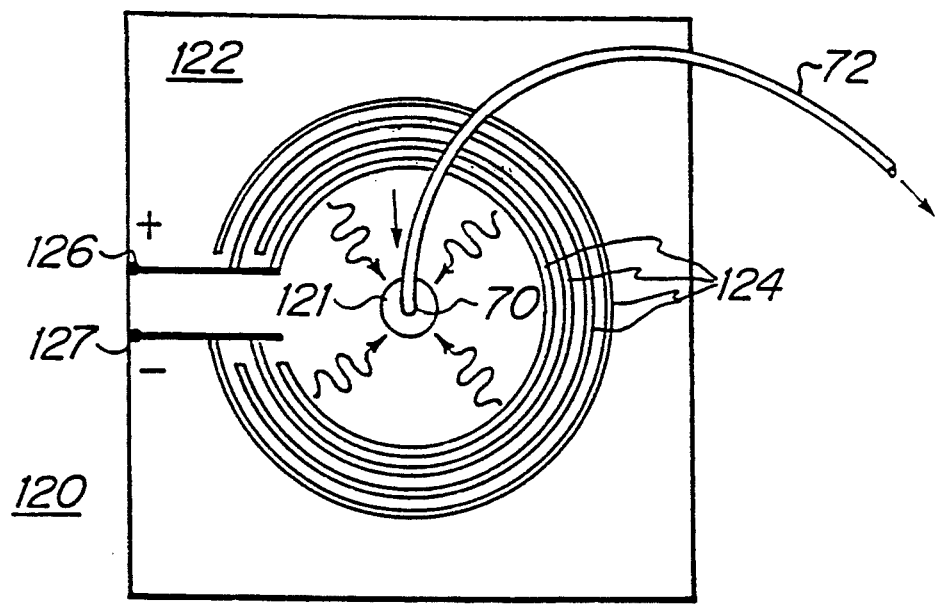
FIG. 9 shows a curvilinear interdigital transducer that generates a single frequency surface acoustic wave.

FIG. 9 shows a single-frequency surface acoustic wave transducer 120 that generates SAW (i.e., surface acoustic wave) as disclosed in copending patent application Ser. No. 07/352,517, entitled *Acoustic Transmission Through Cladded Core Waveguide* discussed earlier. It has a piezoelectric substrate 122 fabricated from a lead-zirconate-titante material commonly referred to as "PZT". Other piezoelectric substances such as zinc oxide would also be suitable. When the thickness of piezoelectric substrate 122 is more than one hundred wavelengths of the acoustic signal generated, then the acoustic waves will primarily propagate along the top surface of piezoelectric substrate 122.

Circular interdigital conductors 124 are metallized stripes that are vacuum deposited onto piezoelectric substrate 122 using conventional photolithographic techniques well known to those persons ordinarily skilled in integrated circuit fabrication arts. Generally a one hundred Ångström base layer of chromium and a top layer of gold is used. The thickness of the top layer may be increased to fabricate higher power transducers. Adjacent curvilinear interdigital conductors 124 have opposite polarities and connect to either electrode 126 or electrode 127 that attached to opposite polarity leads of a signal generator (not shown).

Figure 10:
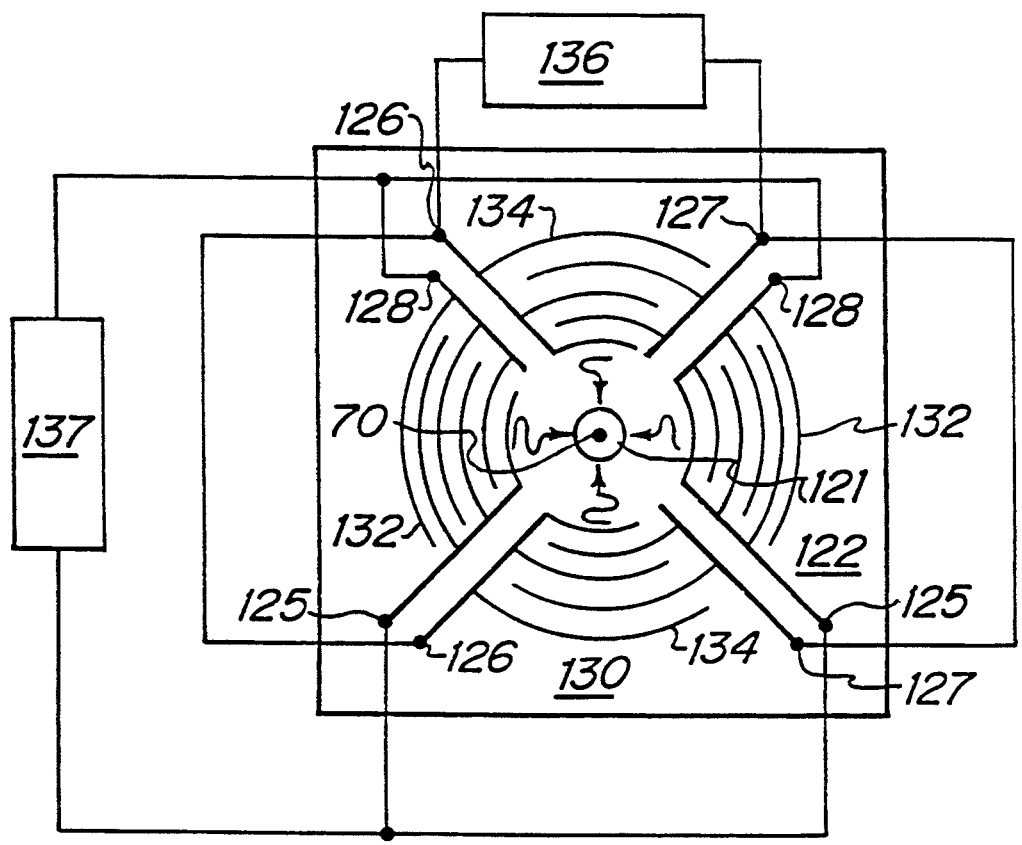
FIG. 10 shows a curvilinear interdigital transducer that generates surface acoustic waves at multiple discrete frequencies and shows a medium for coupling these signals to the acoustic waveguide.

Single-frequency SAW transducer 120 has maximum efficiency when excited by signal whose frequency, $f_o$, satisfies the equation $f_o \times \lambda_o = V_{sw}$ where $V_{sw}$ equals the velocity of surface acoustic waves in piezoelectric substrate 122, $\lambda_o$ equals the distance between curvilinear conductors 124 having the same polarity ($\lambda_o/2$ equals the distance between adjacent curvilinear conductors 124). FIG. 10 shows a multiple-discrete-frequency SAW transducer 130 that connects to an acoustic waveguide (not shown) at focal point 70. It produces surface acoustic waves at multiple discrete frequencies that are converted into bulk/longitudinal waves at focal point 70 by a coupler 121. Most of these bulk/longitudinal waves enter the acoustic waveguide. Like single-frequency SAW transducer 120, shown in FIG. 9, it is constructed upon a piezoelectric substrate 122 and has curvilinear interdigital conductors. To obtain a multiple frequency acoustic signals, the curvilinear interdigital conductor has been split into two sets: curvilinear interdigital conductors for a first frequency 132 and curvilinear interdigital conductors for a second frequency 134. Each set 132, 134 has the shape and is positioned to focus the acoustic waves at focal point 70. The conductors 132, 134 are manufactured the same way as conductors 124 in FIG. 9.

The adjacent conductors of curvilinear interdigital conductors for a first frequency 132 are spaced a distance $\lambda_1/2$ apart and are driven by different electrodes, either electrode 125 or electrode 128 so that adjacent conductors have an opposite polarity. Conductors that are $\lambda_1$ apart connect to the same electrode 125, 128 and have the same polarity. The above described spacing and polarity of the conductors applies to those conductors that are part of curvilinear interdigital conductors for a second frequency 135, except that they connect to electrodes 126, 127. In the preferred embodiment of the invention, push-pull amplifiers 136, 137, which are well known in the art and have the advantage of producing balanced signals that reduces cross talk, excite the transducers formed by curvilinear interdigital conductors for a first frequency 132 and curvilinear interdigital conductors for a second frequency 134 at their resonant frequencies, $$f_1 = \frac{V_{sw}}{\lambda_1} \text{ and } f_2 = \frac{V_{sw}}{\lambda_2},$$

respectively where $V_{sw}$ is the speed of SAW in piezoelectric substrate 122.

In the preferred embodiment of the invention, piezoelectric substrate 122 is thick enough that surface acoustic waves generated by multiple discrete frequency curvilinear interdigital transducer 130 travel along the top surface of piezoelectric substrate 122 until they strike coupler 121 and focus at focal point 70. The velocity of bulk/longitudinal waves, $V_L$, in coupler 121 is less than the velocity of surface waves, $V_{sw}$, so that the surface acoustic waves leak into coupler 121 and become bulk/longitudinal acoustic waves. A fraction of the newly converted longitudinal waves enter the core of the acoustic waveguide (not shown in FIG. 10). The direction of the leaky surface acoustic wave is given by $\theta = \arcsin(V_L/V_{sw})$. If coupler 121 is water, then $\theta \approx 43°$. Materials like Sylgard elastomer, RTV and butyl rubber satisfy this condition.

One choice of frequencies is $f_1$ equals 20 MHz and $f_2$ equals 40 Mhz. At least two additional pairs of curvilinear interdigital conductors could be added to allow use of two additional frequencies so that a multiple discrete frequency curvilinear interdigital transducer 130 could produce acoustic signals at 10, 15, 25, 35 MHz.

Figure 11:
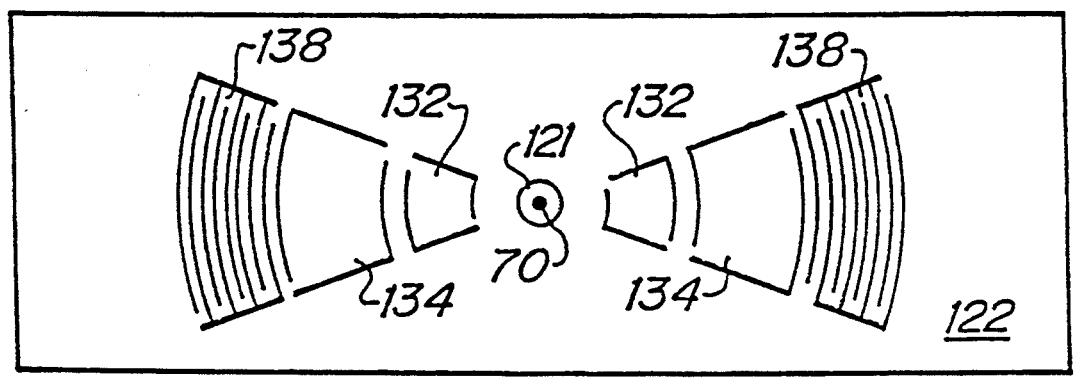
FIG. 11 shows an alternated embodiment of the curvilinear interdigital transducer that generates surface acoustic waves at multiple discrete frequencies and shows a medium for coupling these signals to the acoustic waveguide.

Another embodiment of the present invention, radial transducer 139, is shown in FIG. 11. It has three pairs of curvilinear interdigital conductors 132, 134, 138 on the piezoelectric substrate 122 described above. Conductors 132, 134, 138 are manufactured in the same manner as those described above. Each pair of curvilinear interdigital conductors 132, 134, 138 produces an acoustic signal at a different frequency and all pairs direct their acoustic waves at focal point 70. Three additional pairs of curvilinear interdigital conductors can be added in an orthogonal direction to produce a transducer that generates acoustic signals for a cladded-core acoustic waveguide at six different frequencies. These curvilinear interdigital conductors 132, 134, 138 are manufactured the same way as the curvilinear interdigital conductors in FIGS. 9 and 10.

Figure 12:
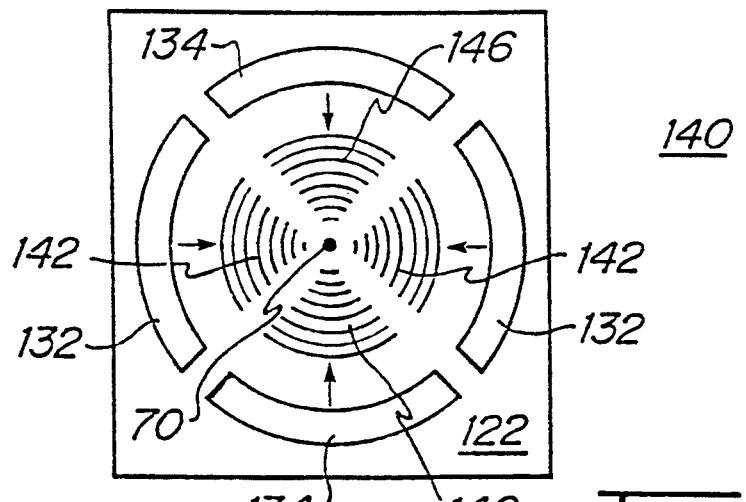
FIG. 12 is a top view of a SAW-BULK acoustic wave transducer.

FIG. 12 shows another embodiment that generates surface acoustic waves and converts them into longitudinal waves before coupling them into the core of the cladded core acoustic waveguide. The longitudinal mode of acoustic waves is the mode desired in cladded-core acoustic waveguides because fluids like blood do not support other waves-they only support long waves. However, surface acoustic wave transducers, such as those in FIGS. 9, 10, 11, and 12 are easier to make and more durable because the frequency of the acoustic wave produced by a surface wave transducer depends upon the spacing of the interdigital conductors which is easily controlled by commonly known photolithographic techniques. With longitudinal wave transducers, such as those shown in FIGS. 1-8, the frequency of the acoustic waves they produce depends on the thickness of the piezoelectric material which is much more difficult to control at the thicknesses required by high frequency acoustic signals. Thus, it is desirable to use a SAW transducer to generate surface acoustic waves and then convert them into longitudinal waves (e.g., in FIGS. 9-11, SAW become leaky waves in a coupler medium whose $V_L$ is less than $V_{sw}$) before coupling them into the acoustic waveguide 72.

Figure 13:
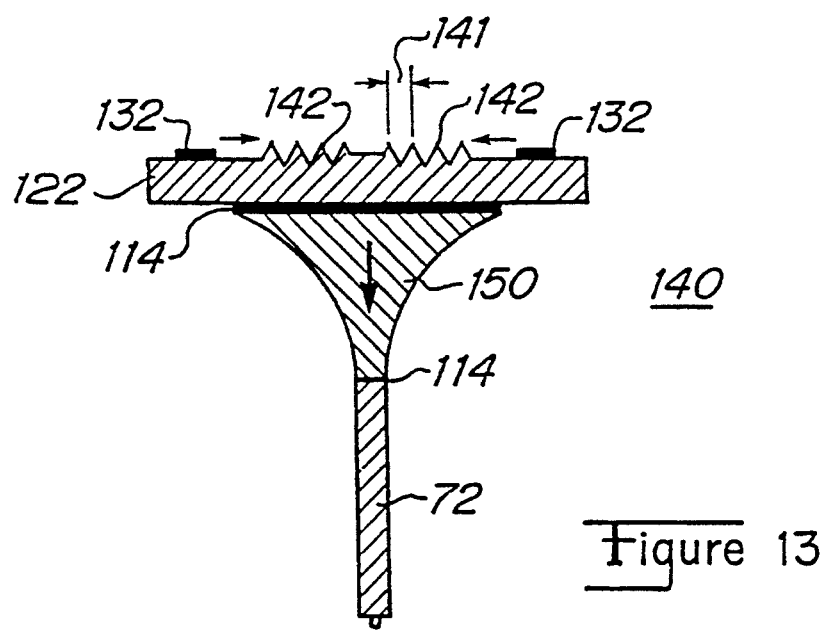
FIG. 13 shows a cross-section of a SAW-BULK acoustic wave transducer coupled to a cladded-core acoustic waveguide.

FIGS. 12 shows a top view and FIG. 13 shows a cross-section of a multiple-discrete frequency SAW transducer with corrugations 140 that is identical to multiple-discrete frequency SAW transducer 130 except that it has a curvilinear corrugations for a first frequency 142 that converts SAW generated by conductors for a first frequency 132 into longitudinal waves and a curvilinear corrugations for a second frequency 146 that converts SAW generated by conductors for a second frequency 134 into longitudinal waves. "Acoustic Bulk-Surface-Wave Transducer" in *Electronics Letters* (May 1, 1969) Vol. 5 No. 9 discusses how bulk and surface waves are strongly coupled at a corrugated surface. FIG. 13 shows a cross-section of a tapered guide 150 that funnels these bulk waves into acoustic waveguide 72.

The curved shape of curvilinear corrugations 142, 146 matches the wavefront of SAW's generated by conductors 132, 134. A peak-to-peak distance 141, shown in FIG. 13, of a curvilinear corrugation 142 equals the wavelength, $\lambda$, of the SAW that encounters it. If the transducer formed by curvilinear interdigital conductors 132 and piezoelectric substrate 122 produces a SAW with a frequency of $f_1$, then the corresponding curvilinear corrugations for a first frequency 142 have a peak-to-peak distance 141 of $V_{sw}/f_1$ where $V_{sw}$ equals the velocity of SAW's in piezoelectric substrate 122.

Figure 14:
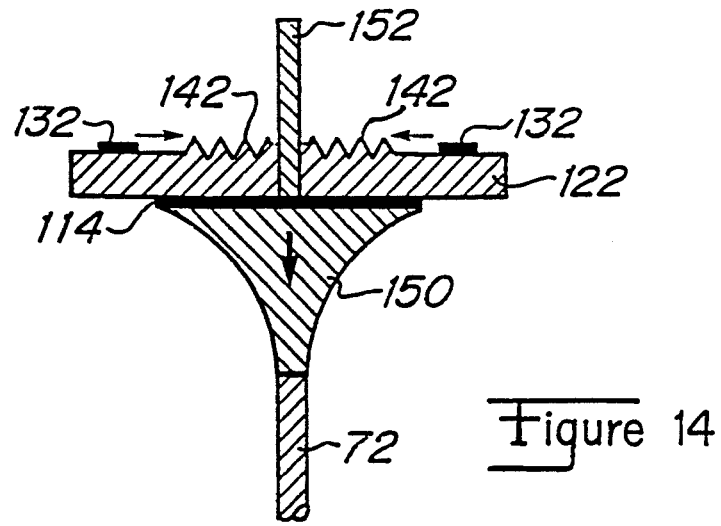
FIG. 14 shows a cross-section of a SAW-BULK acoustic wave transducer that accepts an optical signal.

Curvilinear corrugations 142, 146 are formed by etching or micro machining with a laser. Tapered guide 150 is made from 7075-aluminum and has a matching layer 114 between it and piezoelectric substrate 114 and another matching layer 114 between it and acoustic waveguide 72. FIG. 14 shows an alternate embodiment of present invention that has an optical port 152.

Figure 15:
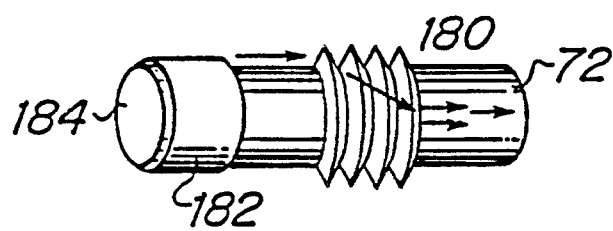
FIG. 15 shows a device that uses corrugations on the acoustic waveguide to couple SAW's to the core of the acoustic waveguide.

FIG. 15 shows an alternate embodiment of the invention that generates SAW's guides them through the cladding to couple them to the core of acoustic waveguide 72. In this embodiment, a SAW transducer 182 is formed by depositing piezoelectric substrate on acoustic waveguide 72 and by photolithographically constructing curvilinear interdigital conductors on piezoelectric substrate. The SAW's generated by transducer 182 travel along the surface of acoustic waveguide 72 until they encounter corrugations 180 that convert the SAW's into bulk/longitudinal waves. This embodiment of the invention can detect echo acoustic waves 106, shown in FIG. 7, by attaching broad band receiver 94 to it. Alternatively, this embodiment transmits optical signals by inserting an optical laser signal at the end.

Figure 16:
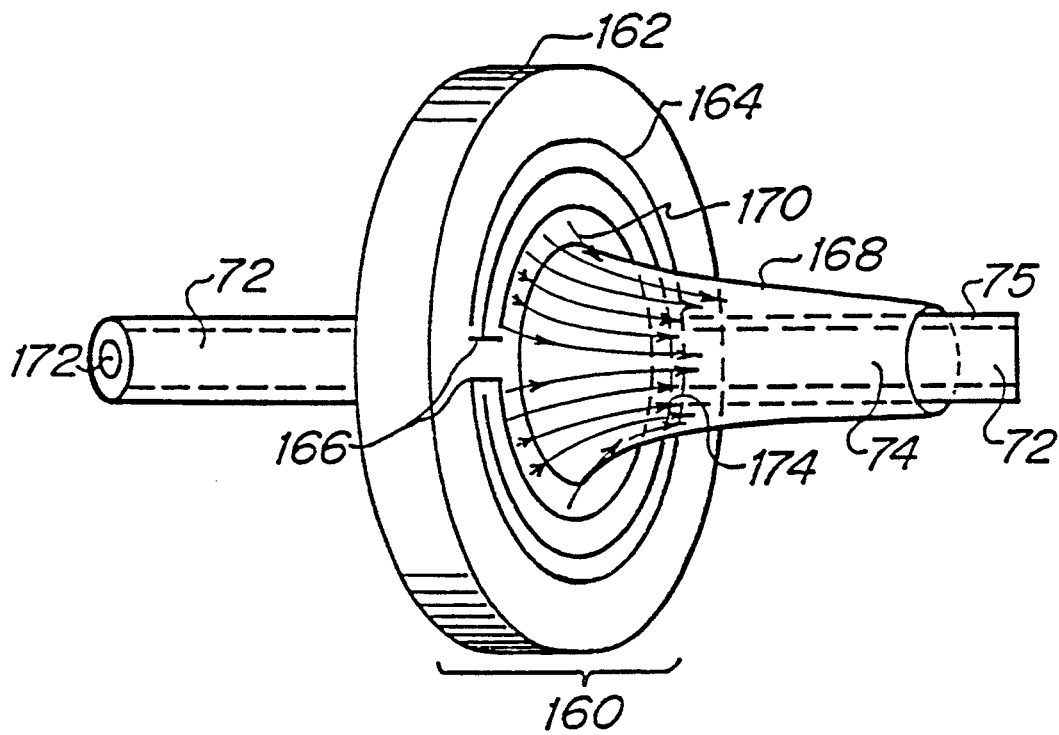
FIG. 16 shows a device that couples SAW to an acoustic waveguide through the cladding.

FIG. 16 shows a SAW transducer 160 and coupling medium 168 for converting the SAW's into leaky waves that pass through cladding 75 to become coupled to core 74 of acoustic waveguide 72. SAW transducer 160 has a piezoelectric disc 162, preferably made out of PZT, and curvilinear interdigital conductors 164 that are driven by an electric signal transmitted by wires 166. Curvilinear interdigital conductors 164 are essentially the same as circular interdigital conductors 124 show in FIG. 9. This embodiment of SAW transducer 160 would generate SAW's at a single frequency. Alternate embodiments of transducer 160 use curvilinear interdigital conductors 132, 134, 138 that are shown in FIGS. 10–14 to generate SAW's at multiple discrete frequencies. Conductors 132, 134, 138 can be arranged as shown in FIG. 10 or as shown in FIG. 11 or any combination of both.

The thickness of piezoelectric substrate 162 should be more than 100 times the wavelength of the SAW so that it travels on the surface of piezoelectric disc 162 a shown by arrows 170. When SAW 170 encounter coupling medium 168, it becomes a leaky longitudinal wave 174 that travels through cladding 75 and eventually into core 74. As described earlier, SAW become leaky longitudinal waves when the velocity of longitudinal waves in the coupling medium, $V_L$, is less than the velocity of SAW in the coupling medium, $V_{SW}$. The acoustic waves change their direction by an angle $\theta$ when they enter coupling medium 168. This angle is equal to $$\theta = \arcsin \frac{V_L}{V_{SW}}.$$

If the coupler is water, then $\theta \simeq 43°$. Commercially available elastomers such as Sylgard, RTV, and butyl rubber satisfy this condition. This embodiment of the invention can detect echo acoustic waves 106, shown in FIG. 7, by attaching broad band receiver 94 to it. Alternatively, this embodiment transmits optical signals by inserting an optical laser signal at the end.

All publications and patent applications cited in the specification are herein incorporated by reference as if each publication or patent application were specifically and individually indicated to be incorporated by reference.

What is claimed is:

1. An apparatus, comprising:
   a. a cladded-core acoustic waveguide having an end at the focal point of an imaginary spherical shell;
   b. a first spherical segment piezoelectric transducer at a first position on the imaginary spherical shell, the first spherical segment piezoelectric transducer generates a first acoustic signal having a first frequency, the first spherical segment piezoelectric transducer focuses the first acoustic signal on the end of the cladded-core acoustic waveguide; and
   c. a second spherical segment piezoelectric transducer at a second position on the imaginary spherical shell, the second spherical segment piezoelectric transducer generates a second acoustic signal having a second frequency, the second spherical segment piezoelectric transducer focuses the second acoustic signal on the end of the cladded-core acoustic waveguide.

2. An apparatus, as in claim 1, wherein:
   a. the first spherical segment piezoelectric transducer further comprises a first spherical annulus piezoelectric transducer; and
   b. the second spherical segment piezoelectric transducer further comprises a second spherical annulus piezoelectric transducer.

3. An apparatus, as in claim 2, further comprising a spherical disc piezoelectric transducer at a third position on the imaginary spherical shell, the spherical disc piezoelectric transducer generates a third acoustic signal having a third frequency and the spherical disc piezoelectric transducer focuses the third acoustic signal on the end of the cladded-core acoustic waveguide.

4. An apparatus, as in claim 2, further comprising a horn having a spherically shaped end adjacent the first spherical segment piezoelectric transducer and the second spherical segment piezoelectric transducer and a narrower end adjacent the cladded-core acoustic waveguide, the horn couples the first acoustic signal and the second acoustic signal to the cladded-core acoustic waveguide.

5. An apparatus, comprising:
   a. a cladded-core acoustic waveguide;
   b. a first piezoelectric transducer having a first set of curvilinear interdigital conductors on a piezoelectric substrate, the first piezoelectric transducer generates a first surface acoustic wave having a first frequency;
   c. a second piezoelectric transducer having a second set of curvilinear interdigital conductors on the piezoelectric substrate, the second piezoelectric transducer generates a second surface acoustic wave having a second frequency; and
   d. a means for coupling the first surface acoustic wave and the second surface acoustic wave into the cladded-core acoustic waveguide.

6. An apparatus, as in claim 5, further comprising:
   a third set of curvilinear interdigital conductors on the piezoelectric substrate that produces a third surface acoustic wave having a third frequency; and
   wherein the means for coupling further comprises a means for coupling the third surface acoustic wave into the cladded-core acoustic waveguide.

7. An apparatus, as in claim 5, wherein the second set of curvilinear interdigital conductors are placed radially behind the first set of curvilinear interdigital conductors.

8. An apparatus, as in claim 5, wherein the means for coupling is a means for converting the first surface acoustic wave and the second surface acoustic wave into leaky longitudinal waves.

9. An apparatus, as in claim 5, wherein the means for coupling the first surface acoustic wave and the second surface acoustic wave into the cladded-core acoustic waveguide, further comprises:

a first set of curvilinear corrugations in the piezoelectric substrate, positioned in a path of the first surface acoustic wave to convert the first surface acoustic wave into a first bulk wave that propagates to the core of the cladded-core acoustic waveguide; and a second set of curvilinear corrugations in the piezoelectric substrate positioned in a path of the second surface acoustic wave to convert the second surface acoustic wave into a second bulk wave that propagates to the core of the cladded-core acoustic waveguide.

10. An apparatus, as in claim 9, further comprising a tapered guide means for funneling the first bulk wave and the second bulk wave into a cladded-core acoustic waveguide.

11. An apparatus, as in claim 9, further comprising a means for inserting an optical beam into the cladded-core acoustic waveguide.

12. An apparatus, comprising:
 a. a cladded-core acoustic waveguide having a cladding surrounding a core;
 b. a means for generating an acoustic signal; and
 c. a means for guiding the acoustic signal through the cladding and into the core of the cladded-core acoustic waveguide.

13. An apparatus, as in claim 12, further comprising an acoustic wave receiver at the end of the cladded-core acoustic waveguide.

14. An apparatus, as in claim 12, further comprising at least one optical port at the end of the cladded-core acoustic waveguide.

15. An apparatus, as in claim 12, wherein the means for generating is a single frequency piezoelectric transducer.

16. An apparatus, as in claim 12, wherein the means for generating is a multiple frequency piezoelectric transducer.

17. An apparatus, as in claim 12, wherein the means for generating further comprises a piezoelectric substrate and conductors.

18. An apparatus, as in claim 12, wherein the coupling medium is at least one corrugation on an exterior surface of the cladded-core acoustic waveguide.

19. An apparatus comprising:
 a. a cladded-core acoustic waveguide having a cladding surrounding a core;
 b. a generating means for generating an acoustic signal;
 c. a guide means for guiding the acoustic signal through the cladding and into the core of the cladded-core acoustic waveguide;
 wherein:
 d. the guide means further comprises a prism positioned between the acoustic waveguide and the generating means.

20. An apparatus, as in claim 19, wherein the prism further comprises a truncated cone and wherein the generating means is a conical annulus piezoelectric transducer positioned on the truncated cone.

21. An apparatus comprising:
 a. a cladded-core acoustic waveguide having a cladding surrounding a core;
 b. a generating means for generating an acoustic signal, including a piezoelectric substrate and conductors;
 c. a guide means for guiding the acoustic signal through the cladding and into the core of the cladded-core acoustic waveguide;
 wherein the conductors further comprise:
 d. a first set of curvilinear conductors on the piezoelectric substrate for producing a first surface acoustic waves of a first frequency; and
 e. a second set of curvilinear conductors on the piezoelectric substrate that produce a second surface acoustic wave of a second frequency.

22. An apparatus, as in claim 12, wherein the means for guiding further comprises a coupling medium that converts surface acoustic waves into leaky longitudinal waves.

23. An apparatus, as in claim 22, wherein the piezoelectric substrate surrounds a portion of the cladded-core acoustic waveguide.

* * * * *